United States Patent [19]

Marcus

[11] Patent Number: 4,958,511
[45] Date of Patent: Sep. 25, 1990

[54] METHOD AND APPARATUS FOR WEAR TESTING ANODIZED SURFACES

[75] Inventor: Leon Marcus, Tonawanda, N.Y.

[73] Assignee: General Motors Corporation, Detroit, Mich.

[21] Appl. No.: 454,474

[22] Filed: Dec. 21, 1989

[51] Int. Cl.$^5$ .............................................. G01N 3/56
[52] U.S. Cl. ........................................................ 73/7
[58] Field of Search ............................... 73/7, 8, 9, 10; 118/712

[56] References Cited

U.S. PATENT DOCUMENTS

| | | | |
|---|---|---|---|
| 2,414,439 | 1/1947 | Brandon | 73/7 |
| 2,962,890 | 12/1960 | Borrino | 73/7 |
| 3,041,868 | 7/1962 | Schaschl et al. | 73/10 |
| 3,834,219 | 9/1974 | Brauer | 73/7 |
| 4,791,807 | 12/1988 | Oechsle | 73/7 |
| 4,864,852 | 9/1989 | Boone | 73/7 |

FOREIGN PATENT DOCUMENTS 0497306 12/1938 United Kingdom ................. 73/10

OTHER PUBLICATIONS

Paper entitled "Measurement of Hardness, Wear Index and Abrasion Resistance of Anodic Coatings on Aluminium" by R. W. Thomas, The British Aluminium Co., Ltd., Gerrards Cross, Buckinghamshire, 1981.

Primary Examiner—Robert Raevis
Attorney, Agent, or Firm—Ronald L. Phillips

[57] ABSTRACT

An anodized aluminum part is wear tested by forcing a ball point stylus against the part and rotating the part about an axis spaced from the stylus. A turntable driven by a motor rotates the part at a desired speed. Weights are used to determine the force on the stylus. A layer of nonconductive oil on the test area helps clear wear debris from the circular wear path due to the motion of the ball through the oil. An ohm meter is connected between the stylus and the aluminum substrate to monitor electrical continuity and thus detect when the stylus wears through the anodized coating. The time required to achieve the wear through is a measure of the wear resistance of the coating.

10 Claims, 1 Drawing Sheet

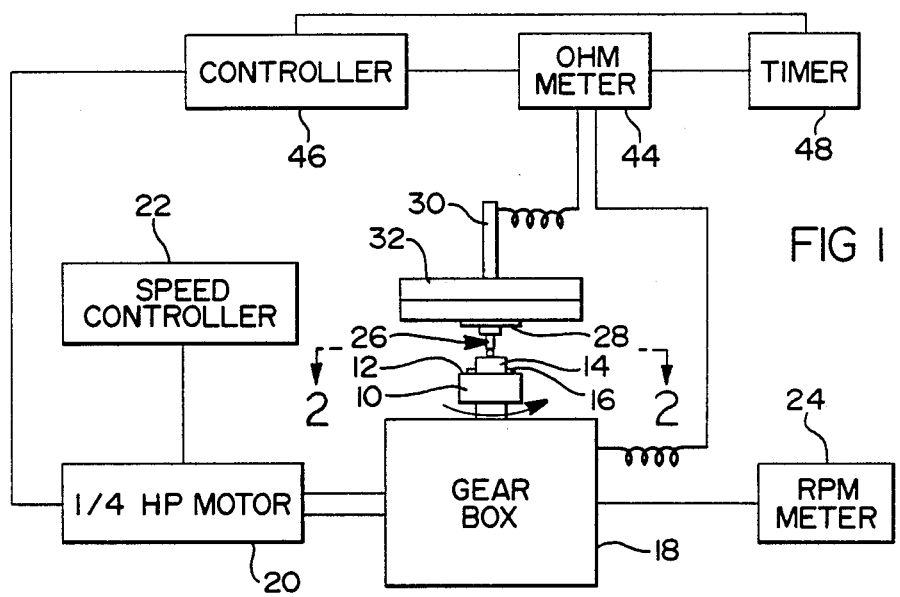
FIG 1
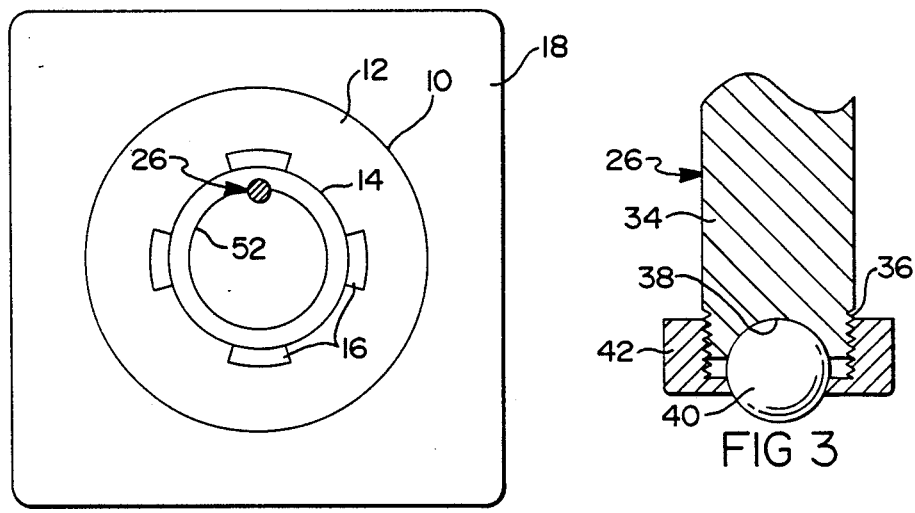
FIG 2
FIG 3
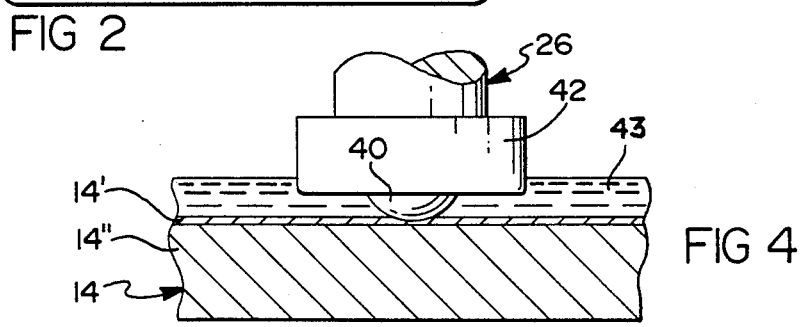
FIG 4

METHOD AND APPARATUS FOR WEAR TESTING ANODIZED SURFACES

FIELD OF THE INVENTION

This invention relates to wear testing and particularly to a method and apparatus for testing an anodized coating on an electrically conductive substrate.

BACKGROUND OF THE INVENTION

Aluminum parts are generally soft and offer poor resistance to wear unless special measures are taken to improve the surface character of the part. Anodized coatings are commonly used for this purpose and provide good protection against wear. The particular type of anodizing process used and the thickness of the coating affect the wear quality of the surface. A "hard anodized" coating is especially useful in offering wear protection to a part. It is important to be able to reliably measure the wear resistance of an anodized coating to assure its suitability for a particular use or to control the anodizing process.

One type of surface wear measurement is the pin-on-disc method which is used to determine the relative wear of two materials. A fixed pin is pressed against a test coupon of material which is rotated on a turntable about an axis spaced from the pin. Strain gages sense the lateral force on the pin to determine the friction force. A track is worn in the coupon surface by the pin and wear measurements are made after a given test time. Pin wear is determined by weight loss measurements and coupon wear is determined by microscopic measurements of the scar width and/or depth. This method has not been used for anodized coatings.

The principal wear testing methods for anodized coatings are described in the paper by R. W. Thomas, "Measurement of Hardness, Wear Index and Abrasion Resistance of Anodic Coating on Aluminum", Transactions of the Institute of Metal Finishing, 1981, Vol. 59, pp 97–104. The tests include indentation tests and abrasion tests. The indentation test is a microhardness test requiring microscope measurement of an indentation made under very low loads on a specially prepared cross-sectional sample of material. The abrasive wear tests include the Taber abraser, abrasive wheel tests, and abrasive jet tests.

The Taber abraser requires a flat sample with a central hole for mounting on a turntable. A pair of freely turning abrasive wheels contact the sample during rotation and scuff the surface. The amount of wear after a given number of test cycles is determined by weight loss measurements or thickness measurements. This test has the problem of wear debris gathering on the wheels and changing the abrasive characteristics of the wheels. The abrasive wheel tests use abrasive paper wrapped on a wheel which is moved back and forth under load across a sample and is periodically indexed to furnish fresh paper. The abrasion debris is continuously cleared from the test site. The abrasive jet method comprises entraining abrasive powder in an air stream and projecting it onto a small area of a sample. The amount of powder required to penetrate a given thickness of material is used as the wear measure.

Each of the abrasion test techniques provides some information on the wear resistance of the anodized surface although they do not necessarily agree quantitatively. Nor is each test necessarily consistent. One variable is the abrasive materials used for the tests which are variable even when they are within specifications. A common feature of these abrasion test is that they deal only with removal of particles by shear in the plane of the surface or at a small angle to the surface. There is no measurement of shear normal to the surface. According to the Thomas paper, general tests can indicate the relative merit of anodized surfaces, but local circumstances are of overriding importance and only tests which closely simulate service conditions provide the correct answers. That is, the test of a material used for a particular part should be designed to address the type of failure experienced by that type of part.

A type of wear not addressed in the above tests is that due to shear normal to the surface such as where a localized pressure crushes the hard coating. This occurs, for example, when a connecting rod ball rides on a mating spherical anodized surface of an aluminum piston and transfers a large force through a localized contact area. It is desirable to have a wear test for this phenomenon which is accurate and reproducible.

SUMMARY OF THE INVENTION

It is therefore an object of the invention to provide a method and apparatus for reproducibly testing for wear in an anodized coating. It is a further object to provide a method and apparatus for testing for wear due to crushing of an anodized coating.

The invention is carried out by the method of wear testing the anodized surface of an electrically conductive part comprising the steps of: rotating the part about an axis of rotation at a set speed, pressing a stylus against the anodized surface of the part at a fixed load and at a given distance from the axis of rotation, whereby a circular path is worn in the surface, testing for electrical continuity between the stylus and the conductive part while the part is rotating, and measuring the time required to attain electrical continuity, wherein the time is a measure of the anodized surface quality.

The invention is further carried out by a wear test apparatus for testing the anodized surface coating on an electrically conductive substrate comprising: means for rotating the substrate about an axis, a stylus for contacting the anodized surface coating at a point spaced from the axis of rotation, means for applying force to the surface coating through the stylus so that during part rotation the stylus wears a path through the surface coating, electrical means for testing continuity between the stylus and the substrate to determine when the stylus contacts the conductive substrate, and timer means for measuring the time required to wear through the anodized coating.

BRIEF DESCRIPTION OF THE DRAWINGS

The above and other advantages of the invention will become more apparent from the following description taken in conjunction with the accompanying drawings wherein like references refer to like parts and wherein:

FIG. 1 is a schematic diagram of the test apparatus according to the invention,

FIG. 2 is a sectional view of the test apparatus taken along line 2—2 of FIG. 1, FIG. 3 is a detail view of the stylus used in the apparatus of FIG. 1, and FIG. 4 is an enlarged view of a stylus in contact with a workpiece during testing according to the invention.

DESCRIPTION OF THE INVENTION

The method and apparatus of the invention were developed specifically for use in testing a hard anodized aluminum piston for a refrigeration compressor where the piston surface is subject to a localized force which has the potential to crush the anodized coating. While the ensuing description is directed to that application it has more general application. While it is preferred to perform the test on an actual part, a specially prepared test sample could be used. The test is applicable to materials other than aluminum. The main requisite is that the material be electrically conductive and its coating be nonconductive. Magnesium is believed to be such a material.

As shown in FIGS. 1 and 2, a rotary stage 10 having a horizontal top 12 and mounted for rotation about a vertical axis supports an anodized aluminum piston or other anodized part 14 which is preferably centered on the axis of rotation. Clamps 16 secure the part 14 to the stage 10. The part is prepared for clamping by removing sufficient anodized coating to assure electrical grounding of the aluminum substrate of the part through the clamp 16 or the stage 10. As further shown in FIG. 1, the stage 10 is supported by and turned by a gear box 18 which is driven by a ¼ horsepower electric motor 20. The gearbox is a speed reducer to yield an output speed on the order of 20 rpm. A motor speed controller 22 is coupled to the motor 20 to adjust the motor speed and an rpm meter 24 attached to the gear box 18 gives a reading of the output speed. A vertically oriented stylus 26 contacts the surface of the part 14 at a point spaced from the axis of rotation such that during rotation of the part 14 the stylus traces a circular path on the top of the part. A support 28 spaced above the part 14 holds the stylus in position and further holds an upwardly extending post 30. Weights 32 with central holes slidably fit over the post and are carried by the support 28 in a position directly above the point of the stylus 26.

The stylus 26, as shown in FIG. 3, consists of a vertical shaft 34 with exterior threads 36 at the lower end, a hemispherical socket 38 in the lower end for receiving a hardened steel ball 40 and a cap 42 threaded onto the shaft threads 36 for holding the ball 40 in the socket tightly enough to prevent ball rotation. The ball 40 is stainless steel having a hardness of Rockwell C 60 to 64. FIG. 4 shows the stylus 26 in place against the anodized coating 14' which covers the substrate 14" of the part 14. A layer 43 of oil sufficiently thick to immerse the ball 40 covers the part 14. The oil must be nonconductive and preferably is a nonhygroscopic petroleum oil containing less than 50 ppm of water.

An electrical aspect of the apparatus includes an ohm meter 44 having one terminal connected to the stylus 26 via the post 30 and the other terminal connected to the aluminum substrate of the part 14 via the gear box 18 and stage 10. The ohm meter 44 is coupled to a controller 46 which in turn is connected to the motor 20 and a timer 48. The controller 46 turns the motor 20 on at the beginning of a test and, in response to a preset resistance reading on the ohm meter 44, turns the motor off to end the test. The timer 48 is also triggered on and off by the controller 46 and records the duration of the test.

The test, as applied to an aluminum piston about 1¼ inches in diameter and having a hard anodized coating 0.001 inch thick, comprises clamping the part to the stage 10 to assure secure mechanical and electrical connection, using a stylus with a 1/16 inch diameter ball 40 placed ½ inch from the stage axis of rotation, loading the stylus with 12 pounds of weights 32, applying a layer 43 of oil, and rotating the stage at 20 rpm. The ball 40 is held against rotation and thus slides along a circular path to wear a groove 52 (FIG. 2) in the anodized coating. Initially the resistance across the coating 14' as determined by the ohm meter 44 is infinite but falls to a low value when the ball wears through the coating and contacts the substrate. It has been found that a higher resistance reading is rendered during part rotation relative to a stationary reading. A reading of 2000 ohms during rotation is indicative of wear through. This corresponds to about 6 ohms for a static reading. The test is terminated when the 2000 ohm reading is attained and the time of the test duration is recorded. The time is a measure of the wear resistance of the coating when all other parameters are the same. Alternatively, the number of revolutions of the part during the test can be used as the wear measure instead of time; a count of the number of rotations is equivalent to a time measure.

The wear mechanism is crushing or shear normal to the surface due to the localized Hertzian force imparted by the loaded ball. Wear debris is generated and is removed from the wear path so that abrasion by the wear particles does not introduce another wear variable. The wear debris is swept from the path of the ball by the motion of the ball through the oil. The use of the layer of oil rather than a dry surface greatly enhances the reproducibility of the test results.

It is important to use the hard ball to minimize ball wear during a test so that the test conditions do not change. A new ball is used for each test or the ball is rotated in the holder prior to each test to provide a new ball surface at the contact point. Test times are kept short to minimize ball wear during a test. The test time is controlled by the weight applied. For the described test, the 12 pound weight resulted in a test time less than 5 minutes. The rate of rotation as well as the diameter of the wear path may be chosen for optimum results for each application. It is also feasible to run more than one test on the same part by running each test at a different diameter wear path. The 1/16 inch ball leaves a narrow wear scar and thus facilitates multiple tests per part. When different path diameters are used, the time results are not directly comparable since different linear surface speeds are involved. Thus appropriate adjustments are to be made when comparing or combining data from different diameters. It is significant, however, that the test is so reproducible that generally a single test per part is adequate to characterize the quality of the anodized coating.

The embodiments of the invention in which an exclusive property or privilege is claimed are defined as follows:

1. The method of wear testing the anodized surface coating of an electrically conductive part comprising the steps of:
    rotating the part about an axis of rotation at a set speed,
    pressing a stylus against the anodized surface coating of the part at a fixed load and at a given distance from the axis of rotation, whereby a circular path is worn in the surface,
    testing for electrical continuity between the stylus and the conductive part while the part is rotating, and measuring the time required to attain electrical continuity, wherein the time is a measure of the anodized surface coating quality.

2. The method as defined in claim 1 including the step of coating the anodized surface coating with nonconductive oil.

3. The method as defined in claim 1 wherein the surface wear mechanism is the crushing of the anodized surface coating by forceful point contact of the stylus on the anodized surface coating; including the step of assuring the integrity of the wear mechanism by continually clearing wear debris from the path.

4. The method as defined in claim 3 wherein the step of assuring the integrity of the wear mechanism comprises coating the anodized surface coating with a layer of nonconductive oil, whereby the wear debris is swept away by the motion of the stylus through the oil.

5. The method as defined in claim 1 wherein the step of pressing the stylus against the anodized surface coating comprises exerting sufficient force on the stylus to crush the anodized surface coating upon repeated traversing of the circular path.

6. A wear test apparatus for testing the anodized surface coating on an electrically conductive substrate comprising:
 means for rotating the substrate about an axis,
 a stylus for contacting the anodized surface coating at a point spaced from the axis of rotation,
 means for applying force to the anodized surface coating through the stylus so that during part rotation the stylus wears a path through the surface coating,
 electrical means for testing continuity between the stylus and the conductive substrate to determine when the stylus contacts the substrate, and
 means for measuring the time required by the stylus to wear through the anodized surface coating.

7. The apparatus as defined in claim 6 wherein the means for rotating the substrate comprises a rotatable stage, a motor for rotating the stage, and a speed reducing mechanism coupling the motor to the stage.

8. The apparatus as defined in claim 6 wherein the stylus comprises a hardened steel ball and a holder for holding the ball against rotation so that sliding contact occurs between the ball and the anodized surface coating.

9. The apparatus as defined in claim 6 wherein the means for applying force comprises a support connected to the stylus and weight means mounted on the support directly above the locus of contact of the stylus and the anodized surface coating.

10. The apparatus as defined in claim 6 wherein the means for rotating the substrate includes clamp means to hold the substrate and also provide an electrical coupling to the substrate, and the said electrical means for testing continuity comprises means coupled to the stylus and to the means for rotating the substrate for monitoring the electrical resistance therebetween.

* * * * *